(12) United States Patent
Fuchs

(10) Patent No.: US 11,197,801 B2
(45) Date of Patent: Dec. 14, 2021

(54) SECURING DEVICE FOR SECURING AN INFUSION APPLIANCE

(71) Applicant: B. BRAUN MELSUNGEN AG, Melsungen (DE)

(72) Inventor: Jürgen Fuchs, Bad Emstal (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 423 days.

(21) Appl. No.: 15/935,905

(22) Filed: Mar. 26, 2018

(65) Prior Publication Data
US 2018/0280238 A1 Oct. 4, 2018

(30) Foreign Application Priority Data

Mar. 28, 2017 (DE) .................... 10 2017 205 188.4

(51) Int. Cl.
*A61M 5/14* (2006.01)
*A61J 1/20* (2006.01)

(52) U.S. Cl.
CPC .............. *A61J 1/2055* (2015.05); *A61J 1/201* (2015.05); *A61J 1/2068* (2015.05); *A61M 5/1411* (2013.01); *A61M 5/1415* (2013.01); *A61M 5/1418* (2013.01); *A61M 2209/082* (2013.01)

(58) Field of Classification Search
CPC ........ A61J 1/2055; A61J 1/2068; A61J 1/201; A61M 5/1415; A61M 5/1418; A61M 5/1411; A61M 2209/082; A61M 5/162; A44B 99/00; Y10T 24/44752; Y10T 24/44761; Y10T 137/0318
See application file for complete search history.

(56) References Cited

U.S. PATENT DOCUMENTS

| 4,589,171 | A | 5/1986 | McGill |
| 10,149,937 | B2 | 12/2018 | Hanner et al. |
| 2001/0025671 | A1* | 10/2001 | Safabash .............. A61J 1/2096 141/329 |
| 2003/0121878 | A1* | 7/2003 | Finneran ............ B65D 39/0023 215/247 |

(Continued)

FOREIGN PATENT DOCUMENTS

| CN | 201426880 Y | 3/2010 |
| CN | 201719627 U | 1/2011 |

(Continued)

OTHER PUBLICATIONS

German Search Report for German Application No. 10 2017 205 188.4, dated Aug. 4, 2017 with partial translation, 9 pages.

(Continued)

*Primary Examiner* — Nicholas J Weiss
*Assistant Examiner* — Alessandro R Del Priore

(57) ABSTRACT

A securing device for securing an infusion appliance to an infusion container includes a first fastening element, which is designed in such a way that it is connectable to a fastening region of the infusion container, and a second fastening element, which is arranged at a distance from the first fastening element and which is designed in such a way that it is connectable to a fastening region of the infusion appliance. At least one connection element connects the first fastening element and the second fastening element to each other. The securing device can be used for medical infusion and transfusion arrangements.

11 Claims, 3 Drawing Sheets

(56) References Cited

U.S. PATENT DOCUMENTS

Figure 1:
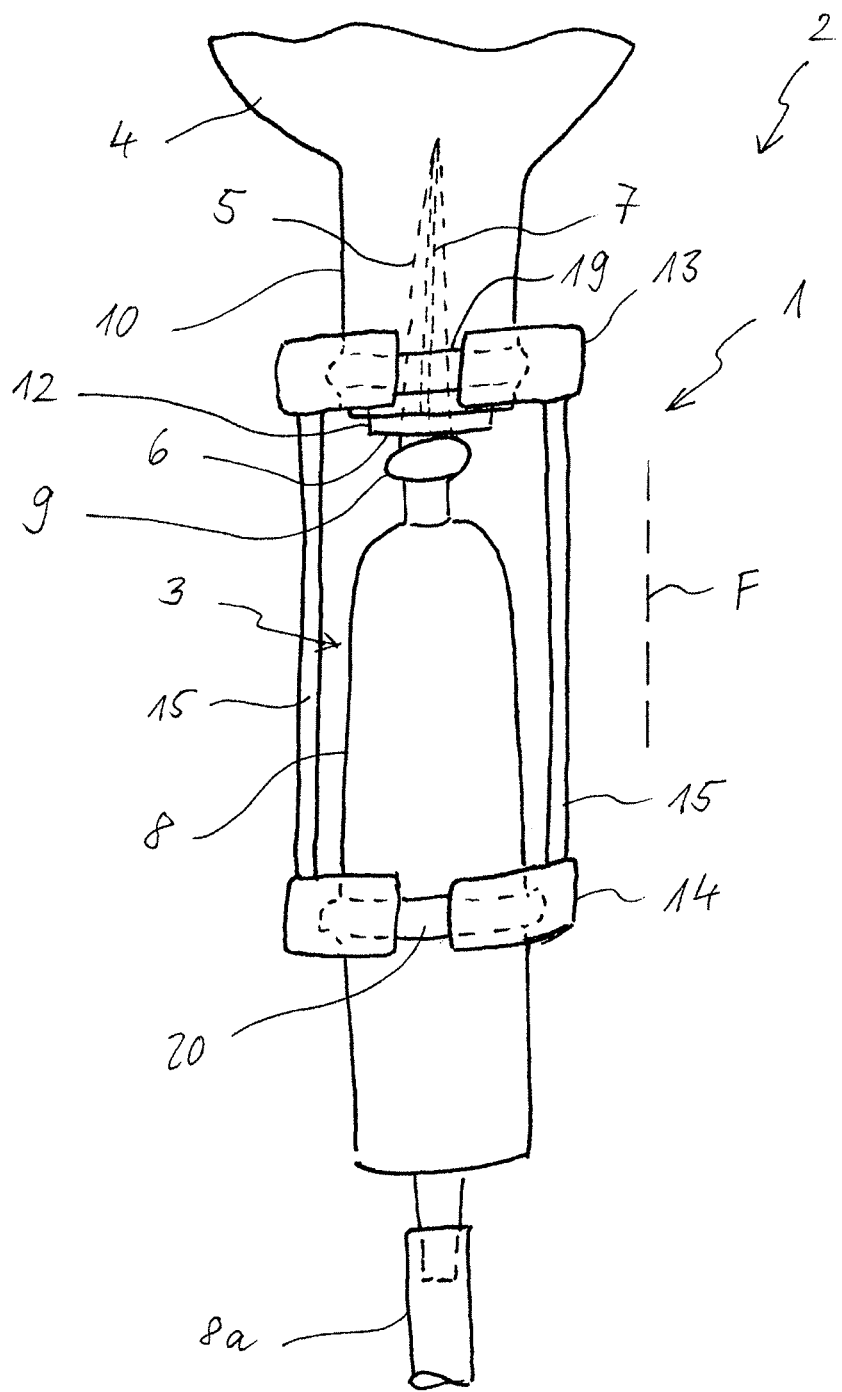

2016/0238048 A1\* 8/2016 Halabi .................. F16B 7/0426
2016/0270816 A1\* 9/2016 Mather .................... A61B 1/07

FOREIGN PATENT DOCUMENTS

| CN | 104758995 A | 7/2015 | |
|----|----|----|----|
| CN | 104884103 A | 9/2015 | |
| DE | 20302788 \* | 6/2004 | ............ A61M 39/10 |
| DE | 20302788 U1 | 6/2004 | |
| JP | H07124264 A | 5/1995 | |
| JP | H07124264 A \* | 5/1996 | ................ A61J 1/05 |
| JP | 09239026 A | 9/1997 | |
| WO | 2011118411 A1 | 9/2011 | |
| WO | 2014000494 A1 | 1/2014 | |
| WO | 2014008832 A1 | 1/2014 | |

OTHER PUBLICATIONS

Extended European Search Report for European Application No. 18 161 565.9, dated Aug. 3, 2018, with partial English translation, 8 pages.
Communication pursuant to Rule 94(3) for European Application No. 18 161 565.9, dated Aug. 6, 2019, 4 pages.
Office Action received in Chinese Application No. 201810266399.6 dated Apr. 30, 2021, with translation, 23 pages.

\* cited by examiner

SECURING DEVICE FOR SECURING AN INFUSION APPLIANCE

RELATED APPLICATION(S)

This application claims the benefit of priority of German patent application DE 10 2017 205 188.4, filed Mar. 28, 2017, the content of which is incorporated by reference in its entirety into this application.

FIELD

The present disclosure relates to a securing device for securing an infusion appliance to an infusion container.

BACKGROUND

Infusion appliances and infusion containers are generally known in the field of medical technology. Such infusion appliances are also designated as infusion systems and serve to provide a liquid-conveying connection between an infusion container and a patient-side access. By means of such a conveying connection, infusion liquid from the infusion container can be introduced into the patient-side access, for example in the context of infusion therapy by pressure or gravity. For fixing to the infusion container, known infusion appliances have a piercing mandrel, for piercing a pierceable region of the infusion container and for leading the infusion liquid out of the latter, and a drip chamber adjoining an end of the piercing mandrel. The drip chamber receives, drop by drop, the infusion liquid conveyed out of the infusion container by means of the piercing mandrel. Moreover, the infusion appliance can have a ventilation mechanism which is arranged between the piercing mandrel and the drip chamber and which permits controlled ventilation of the infusion container, a fluid line arranged downstream from the drip chamber in order to convey the infusion liquid out of the drip chamber, an adjustment mechanism which is operatively connected to the fluid line for the purpose of adjusting the flow of liquid through the fluid line, and a connector piece which is arranged at the outlet side of the fluid line and which connects the fluid line to the patient-side access. Known infusion containers have a bottle shape or bag shape and are provided for receiving an infusion liquid or solution. Such infusion containers have a pierceable region that can be pierced by means of a piercing mandrel of an infusion appliance. In generally known infusion containers, the pierceable region can be provided at an elastic stopper, which can additionally serve as a closure of the infusion container. In order to convey infusion liquid out of the infusion container, the piercing mandrel of the infusion appliance sufficiently pierces the pierceable region from the outside right into the interior of the infusion container. In this way, the infusion liquid can be conveyed via an elongate through-opening of the piercing mandrel into the drip chamber and onwards into the fluid line, and finally through the connector piece into the patient-side access. Here, the infusion appliance and the infusion container are connected mechanically to each other by the frictional engagement acting between the piercing mandrel and the pierceable region and in this way form an infusion arrangement.

SUMMARY

The object of the present disclosure is to achieve improved handling of such an infusion arrangement.

This object is achieved by a securing device for securing an infusion appliance fixed to an infusion container, having a first fastening element, which is designed in such a way that it is connectable to a fastening region of the infusion container, and a second fastening element, which is arranged at a distance from the first fastening element and which is designed in such a way that it is connectable to a fastening region of the infusion appliance, and at least one connection element, which connects the first fastening element and the second fastening element to each other. The present disclosure proceeds from the consideration that an infusion arrangement mechanically connected in a customary manner is disadvantageous in terms of its handling ability. In particular, in some circumstances the substantially frictional connection between piercing mandrel and pierceable region is not sufficient to counteract unwanted separation of the infusion arrangement. If unwanted separation of this kind occurs during infusion therapy, it is not possible to rule out an adverse effect on the patient. By contrast, the securing device according to the present disclosure secures the fixed arrangement in at least one securing direction. For this purpose, the securing device has a first and a second fastening element. These two fastening elements are connected to each other by means of a connection element. The first fastening element is assigned to the fastening region of the infusion container and can be connected mechanically thereto. The second fastening element is assigned to the fastening region of the infusion appliance and can be connected mechanically thereto. In order to secure an infusion arrangement composed of the infusion container and of the infusion appliance fixed to the latter, at least one of the fastening elements is connected to the fastening region assigned to it. Securing in the sense of the present disclosure is to be understood as securing an existing mechanical connection. Such securing can be achieved by a mechanical connection acting in addition to and at the same time as the existing connection or by a passively redundant mechanical connection that replaces the existing connection only in the event of separation. The securing device thus secures against separation in at least one securing direction. A securing direction in the sense of the present disclosure is to be understood as a direction in which a separation of an existing mechanical connection between the infusion container and the infusion appliance is counteracted. If this mechanical connection is formed substantially by frictional engagement between the piercing mandrel of the infusion appliance and the pierceable region of the infusion container, the securing direction runs substantially parallel to the piercing direction of the piercing mandrel into the pierceable region. Thus, according to the present disclosure, the securing device counteracts unwanted separation of the connection between the infusion appliance and the infusion container, for example on account of inadvertent withdrawal of the piercing mandrel from the pierceable region. In this way, it is possible to avoid adversely affecting a patient during the infusion therapy. Accordingly, much improved handling of the infusion arrangement is ultimately achieved.

As has been described above, the solution according to the present disclosure is suitable in a particularly advantageous manner for securing an infusion appliance to an infusion container. However, the solution according to the present disclosure can also be used for securing a transfusion appliance to a transfusion container and can to this extent be used in transfusion therapy.

In one embodiment, at least one of the fastening elements is designed in such a way that, in a fastened state, it engages around the outside of the respective fastening region at least in part and substantially transversely with respect to the securing direction. In this way, a connection to the respective fastening region can be produced easily by hand and in a particularly ergonomic manner. Moreover, the connection of this kind is easy to see and accordingly easy to check. Advantageously, both fastening elements are designed in such a way that, in a fastened state, they engage around the outside of the respective fastening region at least in part and substantially transversely with respect to the securing direction.

In a further embodiment, at least one of the fastening elements is designed in such a way that it is connectable to the respective fastening region with form-fit engagement. Form-fit connections can be dimensioned to take up considerable loads. This is accordingly an embodiment that cuts down on installation space and material. Advantageously, both fastening elements are designed in such a way that they are connectable to the respective fastening region with form-fit engagement.

In a further embodiment, at least one of the fastening elements has a locking element which is connectable to the respective fastening region with force-fit and/or form-fit engagement. Particularly advantageously, the locking element for connection to the respective fastening region is elastically expandable, in particular transversely with respect to the securing direction. To produce the connection, the locking element is elastically expanded and placed on the respective fastening region. The spring action counteracting the elastic expansion causes locking on the fastening region. Accordingly, a reliable connection can be obtained that is particularly easy to produce.

In a further embodiment, the locking element is ring-shaped and has at least one open wall region along its circumferential direction. Advantageously, the locking element is C-shaped with an open wall region.

In a further embodiment, at least one of the fastening elements has a profile which is provided to receive at least one portion of a profile of the respective fastening region. The profiles can be designed to be complementary to each other. A profile in the sense of the present disclosure is to be understood to mean depressions in a wall portion and also projections on a wall portion. Particularly advantageously, at least one of the fastening elements has a groove which is provided to receive at least one portion of a wall projection that extends substantially perpendicularly from the fastening region.

In a further embodiment, the first fastening element is designed in such a way that it is connectable to a neck region of an infusion container configured in the shape of a bottle. For this purpose, it is advantageous for the first fastening element to be substantially ring-shaped and to have an open wall portion in the radial direction, wherein the ring diameter corresponds substantially to the diameter of the neck region. For connection to the neck region, the fastening element is placed with its open wall region radially onto the neck region and radially loaded, wherein the fastening element is elastically widened and finally locked onto the neck region of the infusion container.

In a further embodiment, the second fastening element is designed in such a way that it is connectable to a drip chamber of the infusion appliance. Advantageously, the second fastening element is connectable to a wall portion of the substantially cylindrical drip chamber wall, which wall portion projects radially from the drip chamber wall. A connection between the securing device and the infusion appliance is thus achieved that is particularly easy to produce.

In a further embodiment, the connection element has at least one strut extending between the first fastening element and the second fastening element. In a fastened state of the fixing device, the strut advantageously extends substantially along the fixing direction. In order to ensure a particularly reliable connection of the fastening elements to each other, the connection element advantageously has two struts.

In a further embodiment, the connection element is elastically extensible at least in part. In this way, a non-alignment of the piercing mandrel in the pierceable region or an overshoot along the securing direction through incomplete insertion of the piercing mandrel upon connection of the securing device can be compensated by a corresponding extension of the connection element. This provides securing that is particularly reliable and easy to produce.

In a further embodiment, the first fastening element and the second fastening element and the connection element are formed contiguously in one piece. The securing device is advantageously formed as an injection moulding, in particular from polypropylene. This permits inexpensive manufacture and results in advantageous mechanical properties.

The present disclosure also relates to an infusion arrangement with a drip chamber and/or an infusion container and with a securing device which is configured as described above.

BRIEF DESCRIPTION OF THE DRAWING FIGURES

Further advantages and features will become clear from the following description of a preferred exemplary embodiment set out in the drawings.

Figure 2:
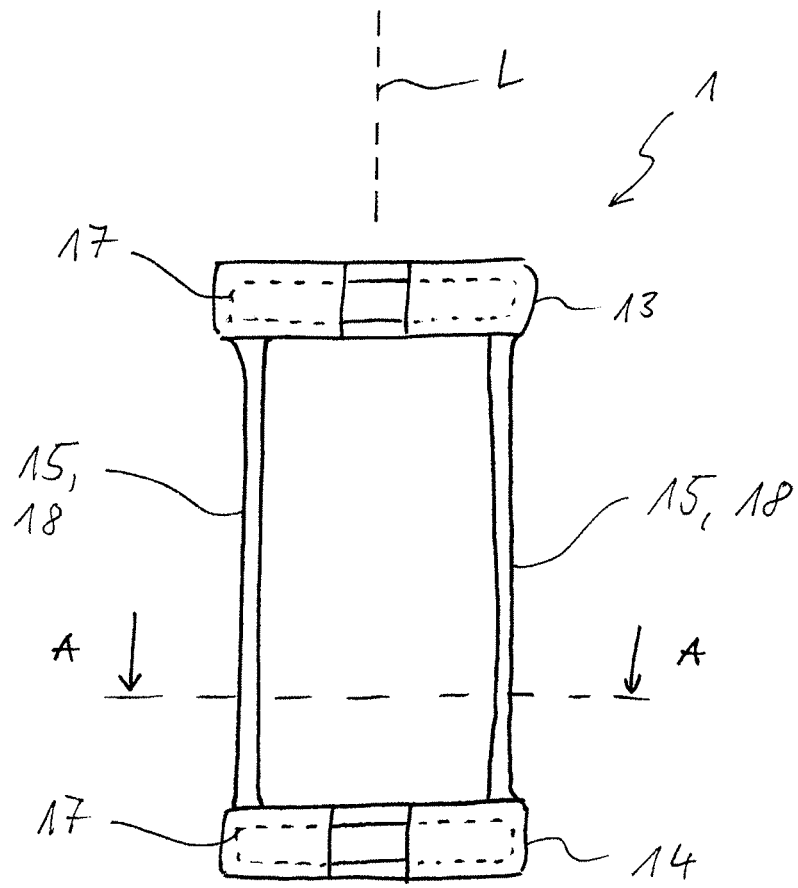
Figure 3:
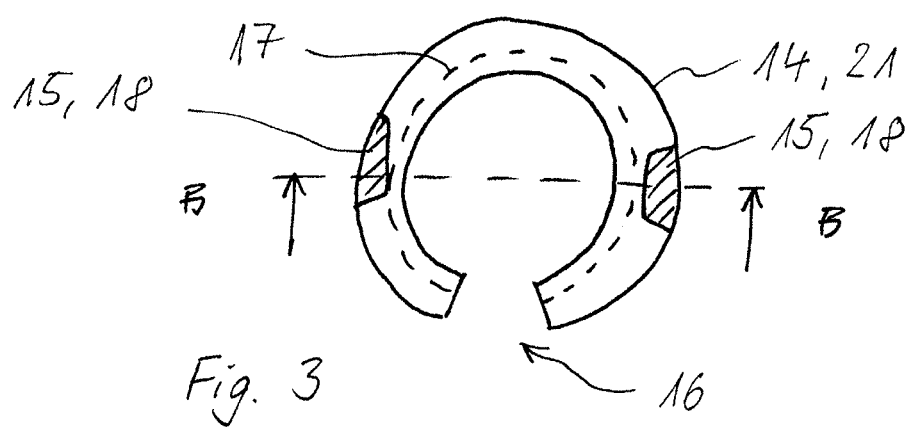
Figure 4:
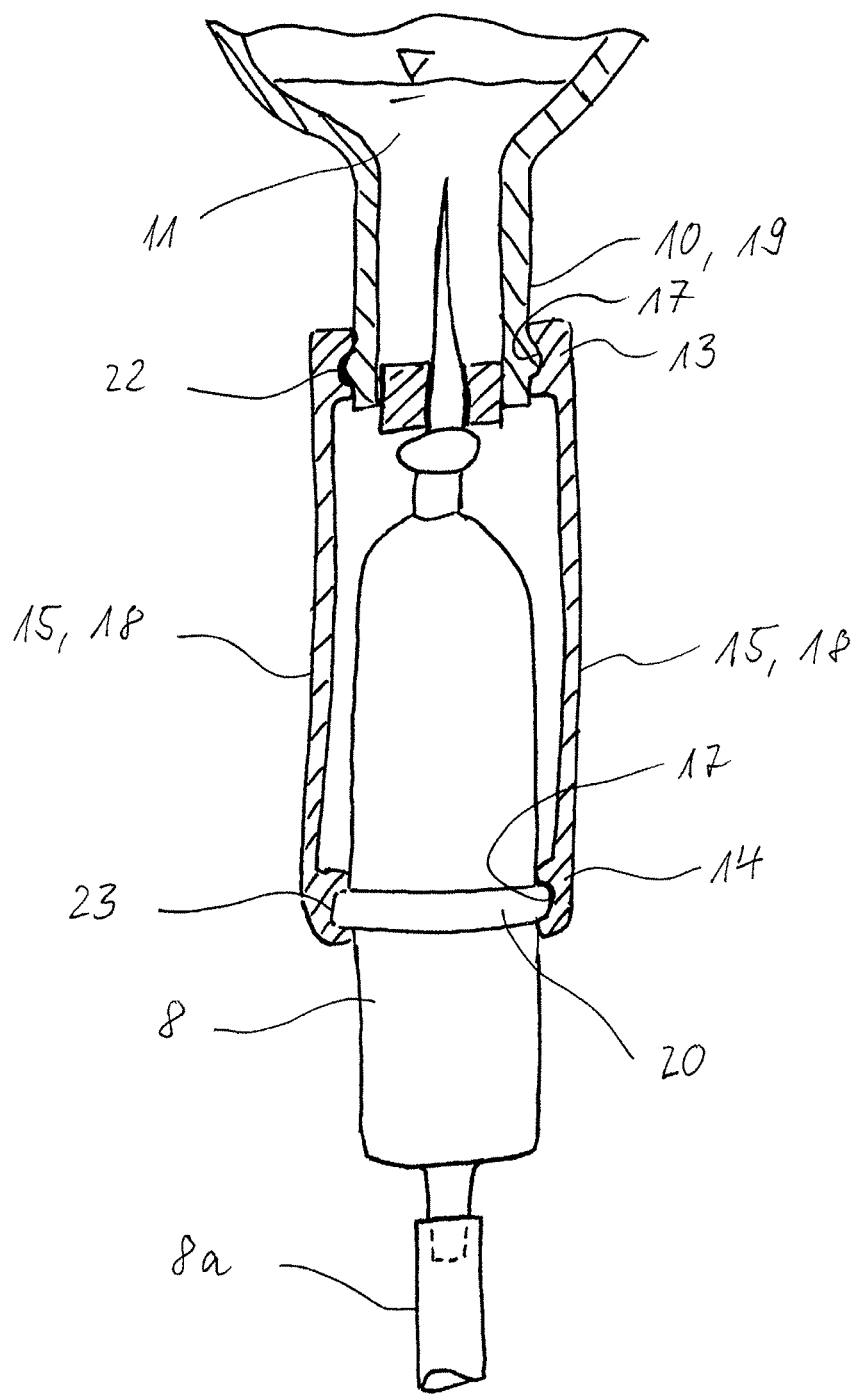

FIG. 1 shows a schematic side view of a detail of an infusion arrangement in the region of the drip chamber, which is secured using a preferred embodiment of a securing device according to the present disclosure, FIG. 2 shows a side view of the securing device from FIG. 1, FIG. 3 shows a further view of the securing device from FIG. 1 and FIG. 2, along a section line A-A according to FIG. 2, and FIG. 4 shows a partially sectioned view of the infusion arrangement together with a securing device from FIG. 1, along a section line B-B according to FIG. 3.

DETAILED DESCRIPTION

A securing device 1 according to FIGS. 1 to 4 is provided for securing an infusion arrangement 2, as can be seen from FIGS. 1 and 4. The infusion arrangement 2, known as such in the field of medical technology, is composed of an infusion appliance 3 and an infusion container 4, wherein for reasons of clarity, the infusion appliance 3 and the infusion container 4 are shown only in part in FIGS. 1 and 4.

The infusion appliance 3, which is also designated as an infusion system, serves to connect the infusion container 4 to a patient-side access (not shown in any detail) in a manner that allows liquid to be conveyed. For example, in the context of infusion therapy by pressure or gravity, a conveying connection of this kind allows infusion liquid from the infusion container 4 to be introduced into the patient-side access. For this purpose, the infusion appliance 3 has a piercing mandrel arranged at one end, which piercing mandrel 5 is provided for piercing a pierceable region 6 of the infusion container 4. The piercing mandrel 5 has an elongate through-opening 7 by means of which infusion liquid can be conveyed out of the interior of the infusion container 4.

Moreover, the infusion appliance 3 has a drip chamber 8 which at one end adjoins the piercing mandrel 5 in the longitudinal direction of the infusion appliance 3 and which is provided to receive infusion liquid drop by drop. In addition, the infusion appliance 3 has a ventilation mechanism 9 arranged between the piercing mandrel 5 and the drip chamber 8, said ventilation mechanism 9 being indicated only schematically in FIGS. 1 and 4. The ventilation mechanism 9 is provided for controlled ventilation of the infusion container 4 during the discharge of infusion liquid. Moreover, the infusion appliance 3 has a fluid line 8a arranged at the outlet side of the drip chamber 8, which fluid line 8a is in the form of an infusion hose and, for reasons of clarity, is shown only in part. In a manner likewise not shown in any detail, the infusion appliance 3 can have an adjustment mechanism operatively connected to the fluid line 8a for the purpose of adjusting the flow of liquid through the fluid line 8a, and a connector piece which is arranged at the outlet side of the fluid line 8a and connects the fluid line 8a to the patient-side access.

The infusion container 4 of the infusion arrangement 2 is known per se and is configured in the shape of a bottle, with FIGS. 1 and 4 showing only a neck region 10 of the infusion bottle. The infusion container 4 is filled with an infusion liquid 11, as can be seen from FIG. 4. The pierceable region 6 of the infusion container 4 is provided at an elastic stopper 12. The elastic stopper 12 also serves to close the infusion container 4 and seals the latter off in an unpierced state of the pierceable region 6. The elastic stopper 12 is designed in such a way that it can be pierced sufficiently by the piercing mandrel 5 of the infusion appliance 3 from the outside into the interior of the infusion container 4.

To produce the fluid-conveying connection between the infusion container 4 and the patient-side access which, as has been described above, is not shown in any detail, the piercing mandrel 5 of the infusion appliance 3 is pushed into the pierceable region 6 of the elastic stopper 12 of the infusion container 4. As soon as the elastic stopper 12 has been pierced all the way through by the piercing mandrel 5, a fluid-conveying connection is produced, such that infusion liquid 11 from the interior of the infusion container 4 can be conveyed via the through-opening 7 into the drip chamber 8 and onwards into the fluid line 8a as far as the patient-side access. Here, the infusion appliance 3 and the infusion container 4 are connected mechanically to each other, i.e. fixed relative to each other, by the frictional engagement between the piercing mandrel 5 and the elastic stopper 12, and in this way they form the infusion arrangement 2. The securing device 1 is provided in particular to counteract an unwanted sliding movement of the piercing mandrel 5 out of the elastic stopper 12.

As can be seen from FIG. 2 among others, the securing device 1 has a first fastening element 13, a second fastening element 14, and two elongate connection elements 15 which connect the first fastening element 13 and the second fastening element 14 to each other. The first fastening element 13 and the second fastening element 14 are arranged one above the other in the longitudinal direction L of the securing device 1 and are substantially coaxial. As can be seen from FIG. 3, the first fastening element 13 and the second fastening element 14 are each ring-shaped and in each case have an open wall region 16 in the circumferential direction, resulting in what is substantially a C-shaped configuration of the fastening elements 13, 14. Consequently, a slight elastic expandability of the fastening elements 13, 14 is obtained in a tangential direction. On their radially inner faces, the fastening elements 13, 14 each have a profile 17. These profiles 17 are each configured as a radial groove. In this way, the fastening elements 13, 14 each form a locking element 21, which is provided for producing a force-fit and/or form-fit connection.

The connection elements 15 of the securing device are each designed as struts 18. These struts 18 each extend, substantially parallel to the longitudinal direction L, from the top of the second fastening element 14 to the underside of the first fastening element 13. Moreover, the struts 18 each have a small wall thickness compared to the fastening elements 13, 14, such that the struts 18 are more easily deformable by comparison. As a result of the band-shaped cross-sectional configuration of the struts 18 as shown in FIG. 3, there is in particular an elastic extensibility of the struts 18 in the longitudinal direction L. Moreover, the first fastening element 13 and the second fastening element 14 and also the struts 18 are formed contiguously in one piece as an injection moulding.

In order to secure the infusion arrangement 2 by means of the securing device 1, the first fastening element 13 is placed with its open wall region 16 onto the neck region 10 of the infusion container 4, wherein the longitudinal axis L of the fixing device 1 is arranged substantially parallel to the longitudinal extent of the drip chamber 8. Moreover, the first fastening element 13 is loaded substantially radially with respect to the neck region 10 and widened tangentially in such a way that the first fastening element 13 is pushed in the radial direction completely over the neck region 10 and locks onto the latter. The neck region 10 in this sense forms a fastening region 19 of the infusion container 4. As can be seen from FIG. 4, a form-fit and force-fit connection acts between the profile 17 on the inner face of the first fastening element 13 and a complementary profile 22 formed on the neck region 10. The first fastening element 13 engages externally around a portion of the fastening region 19, substantially transversely with respect to the securing direction F. Moreover, the second fastening element 14 is connected to the drip chamber 8 of the infusion appliance 3. For this purpose, the second fastening element 14 is placed with its open wall region 16 onto a fastening region 20 of the drip chamber 8. Moreover, the second fastening element 14 is loaded substantially radially with respect to the longitudinal direction of the drip chamber 8 and elastically widened in a tangential direction in such a way that the second fastening element 14 is pushed completely over the fastening region 20 and locks onto the latter. The profile 17 formed on the inner face of the second fastening element 14 and in the shape of a groove at least partially receives a substantially complementary profile 23 provided in the shape of a wall projection. In this way, a form-fit and force-fit connection acts between the second fastening element 14 and the drip chamber 8. The second fastening element 14 engages externally around a portion of the fastening region 20, substantially transversely with respect to the securing direction F. As a result of the securing of the infusion arrangement 2 by means of the securing device 1, it is possible to counteract an unwanted removal of the piercing mandrel 5 of the infusion appliance 3 from the elastic stopper 12 of the infusion container 4 along the securing direction F, which substantially corresponds to the longitudinal direction L of the securing device.

What is claimed:
1. A securing device for securing an infusion appliance fixed to an infusion container in a securing direction, the securing device having a first element including a first radial side, a second radial side, in a first radial groove configured to engage a complementary profile in a fastening region of the infusion container, a second fastening element including a first radial side, a second radial side, and a second radial groove configured to engage a complementary profile in a fastening region of the infusion appliance, the second fastening element arranged at a distance from the first fastening element, and at least one connection element, which connects the first fastening element and the second fastening element to each other, the at least one connection element having a first elastically extensible strut extending between the first radial side of the first fastening element and the first radial side of the second fastening element and a second elastically extensible strut extending between the second radial side of the first fastening element and the second radial side of the second fastening element, and wherein each of the fastening element has a locking element which is connectable to the respective fastening regions with a force fit and/or form-fit engagement, the locking element of each fastening element is a ring-shaped locking element and has at least one open wall region along its circumferential direction, wherein the first and second fastening elements are configured to slide transversely with respect to the securing direction, such that respective fasting regions slide through said open wall region into engagement with the first and second fastening elements.

2. The securing device according to claim 1, wherein at least one of the fastening elements is configured, in a fastened state, to engage around the outside of the respective fastening region at least in part and substantially transversely with respect to a securing direction.

3. The securing device according to claim 1, wherein at least one of the fastening elements is configured to connect to the respective fastening region with form-fit engagement.

4. The securing device according to claim 1, wherein at least one of the fastening elements has a profile which is provided to receive at least one portion of a profile of the respective fastening region.

5. The securing device according to claim 1, wherein the first fastening element is configured to connect to a neck region of an infusion container configured in the shape of a bottle.

6. The securing device according to claim 1, wherein the second fastening element is configured to connect to a drip chamber of the infusion appliance.

7. The securing device according to claim 1, wherein the first radial sides are opposite the second radial side of the respective first and second fasting elements.

8. The securing device according to claim 1, wherein the first fastening element and the second fastening element and the connection element are formed contiguously in one piece.

9. An infusion arrangement with a drip chamber and the infusion container, comprising a securing device according to claim 1, wherein the infusion appliance includes the drip chamber and the complementary profile in the fastening region of the infusion appliance is on the drip chamber.

10. The securing device according to claim 9, wherein each of the first and second struts are elastically extensible in a longitudinal direction.

11. A securing device for securing an infusion appliance to an infusion container in a securing direction, the securing device comprising: a first fastening means for connecting to a fastening region of the infusion container substantially transversely with respect to the securing direction, the first fastening means including a first radial side and a second radial side; a second fastening means for connecting to a fastening region of the infusion appliance, the second fastening means arranged at a distance from the first fastening means substantially transversely with respect to the securing direction, the second fastening means including a first radial side and a second radial side; and at least one connection means for connecting the first fastening means to the second fastening means, the at least one connection means having a first elastically extensible strut extending between the first radial side of the first fastening means and the first radial side of the second fastening means and a second elastically extensible strut extending between the second radial side of the first fastening means and the second radial side of the second fastening means; wherein each of the fastening means has a locking element which is connectable to the respective fastening region with a force fit and/or form-fit engagement, the locking element of each fastening means is a ring-shaped locking element and has at least one open wall region along its circumferential direction, wherein the first and second fastening means are configured to slide transversely with respect to the securing direction, such that the respective fastening regions slide through said open wall region into engagement with the first and second fastening elements.

* * * * *